United States Patent [19]
VanderPol et al.

[11] Patent Number: 5,738,268
[45] Date of Patent: Apr. 14, 1998

[54] METHOD FOR PREPARING TUBE WELD SAMPLE FOR INTERNAL VISUAL INSPECTION

[75] Inventors: Jerald VanderPol, Shingle Springs; Clement Tremblay, Citrus Heights, both of Calif.

[73] Assignee: TRI Tool Inc., Rancho Cordova, Calif.

[21] Appl. No.: 623,571

[22] Filed: Mar. 28, 1996

[51] Int. Cl.$^6$ .............................. B23K 31/12; G01N 3/20
[52] U.S. Cl. .................... 228/103; 29/407.01; 72/324; 73/850; 83/54; 83/581; 83/919
[58] Field of Search .................... 83/23, 54, 581, 83/919; 72/324; 228/103, 105; 73/850; 29/407.01, 407.04

[56] References Cited

U.S. PATENT DOCUMENTS

| | | |
|---|---|---|
| 3,881,385 | 5/1975 | Coy ........................ 83/581 X |
| 3,892,089 | 7/1975 | Coulstring . |
| 3,906,784 | 9/1975 | Coulstring . |
| 4,653,370 | 3/1987 | Baudisch et al. ................. 83/581 X |

*Primary Examiner*—Eugenia Jones
*Attorney, Agent, or Firm*—Bacon & Thomas

[57] ABSTRACT

A process for preparing tubular coupons formed of a pair of tube lengths butt-welded together with a full depth circumferential weld includes partially diagonally cutting the coupon sample through its transverse dimension so as to leave a thin bending strip along one wall of the coupon about which the coupon is bent for inspection of the internal surface of the weld area. Two procedures are described, both of which leave the interior surface of the weld exposed adjacent the diagonal cutting line through the coupon. The procedure facilitates bending open the cut coupon for internal inspection of the weld area. A jig fixture for holding the coupon during cutting by a band saw blade is described.

7 Claims, 5 Drawing Sheets

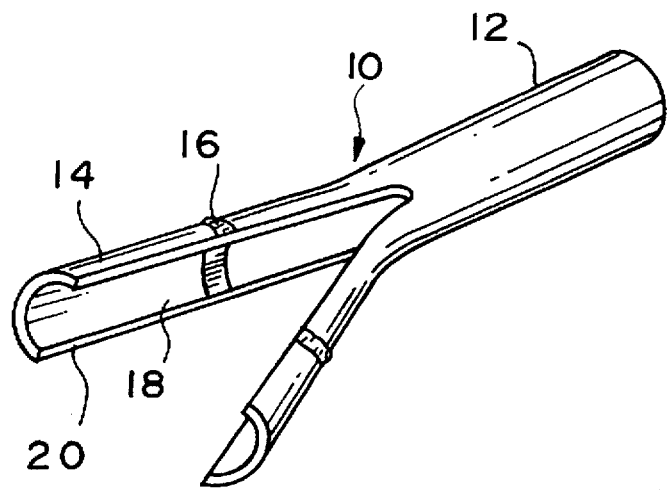
FIG_1
PRIOR ART
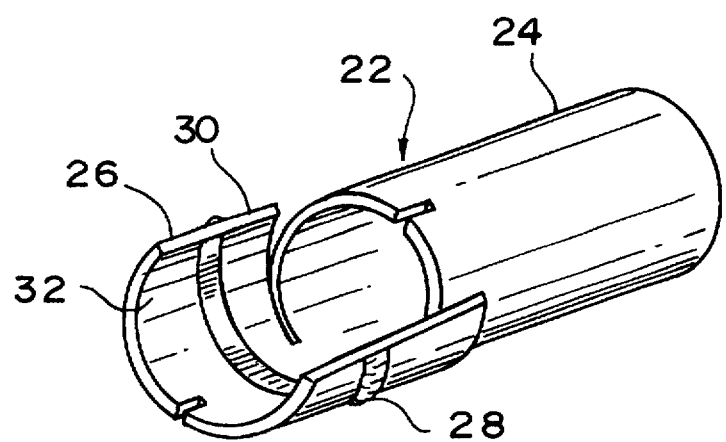
FIG_2
PRIOR ART

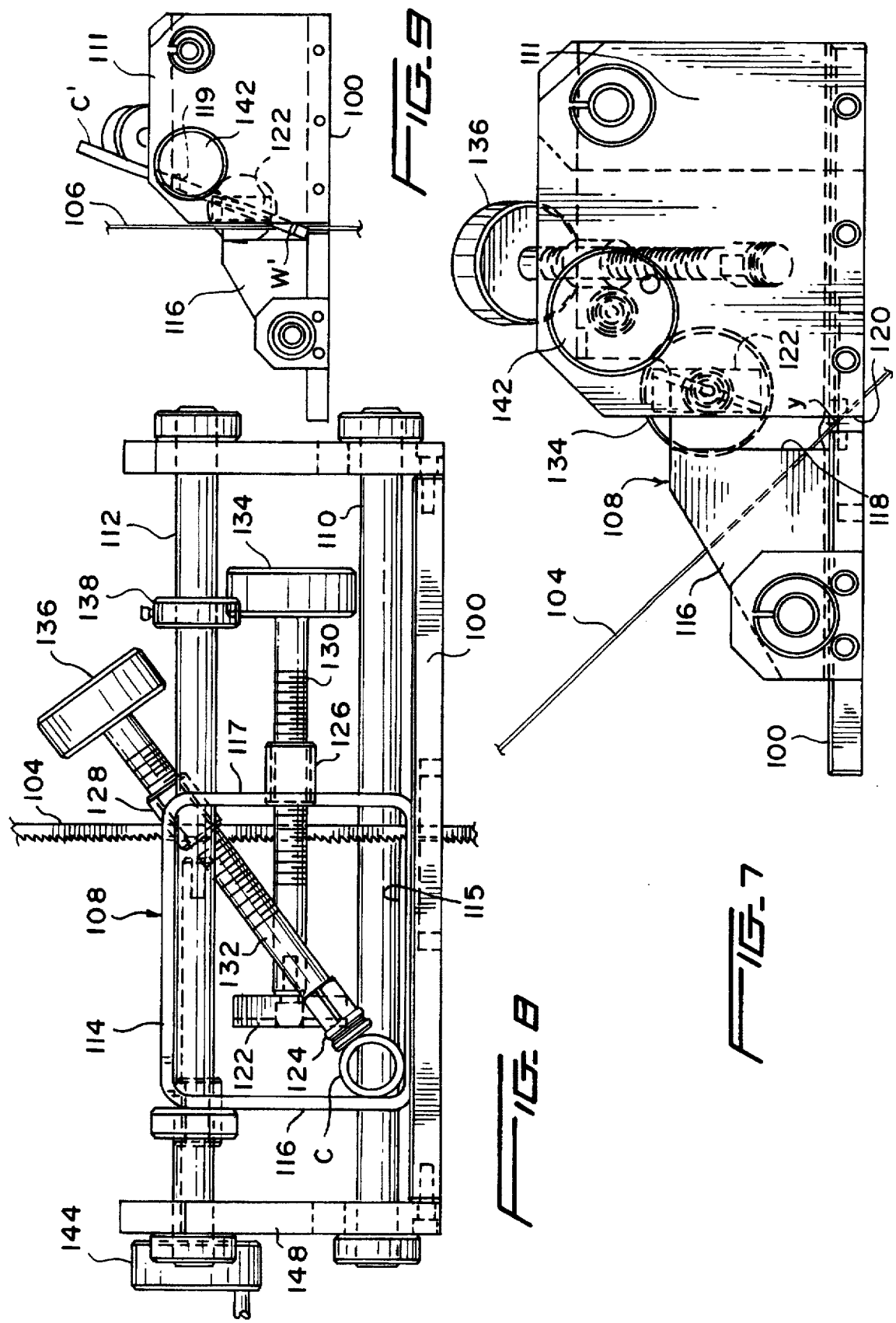

METHOD FOR PREPARING TUBE WELD SAMPLE FOR INTERNAL VISUAL INSPECTION

FIELD OF THE INVENTION

This invention relates to the field of preparation of welded samples of tubing for internal visual inspection and certification.

BACKGROUND OF RELATED INFORMATION

Inspection and certification of welds is a necessary and customary practice to a varying degree depending upon the criticality of the strength and purity of the weld joint and the particular industry or environment in which the welding operation is carried out. In some cases, examples of welds performed on butt-welded tubing joined by circumferential full depth welds must be inspected within the welded tubing to ensure that the depth of the weld is proper and that the interior of the tubing and weld conforms to specifications in the weld area. Indeed, in some industries and in accordance with specifications promulgated with respect to such industries, statistical samples of tubular welded joints performed in accordance with a particular specification must be visually inspected internally and otherwise to ensure that the samples and the welds meet the specification. Such samples of welds are called "coupons" or "coupon samples" and such samples are retained after inspection along with appropriate records pertaining to the sample for verification purposes. The periodic inspection of weld samples may be carried out throughout a work shift or in follow-up to a work shift, but such samples in any event must be processed rapidly and efficiently when a large number of samples must be prepared for inspection, inspected and certified.

U.S. Pat. No. 3,906,784 and U.S. Pat. No. 3,892,089 described two examples of weld coupon sample preparation systems involving butt-welded plates that are systematically cut and bent to test welded joints. Tubular circumferential weld samples, on the other hand, are not typically tested or certified for strength but rather are visually inspected both externally and internally of the welded tube length to verify that weld fusion penetration is complete and free of impurities.

The process of cutting open a weld coupon sample in accordance with the prior art is illustrated in FIGS. 1 and 2 of the appended drawings and will be discussed in detail below in the detailed description of the invention. However, in general, the prior art envisions slitting the tubular weld samples longitudinally through the circumferential weld area, bending open the sample and then visually inspecting the weld on the interior of the coupon sample to verify the quality of the weld. If the tubing is small in diameter and relatively thin-walled, a simple longitudinal slit along the diameter of the tube can be effectively made without undue difficulty provided that care is taken to avoid injury to the worker performing the cutting of the coupon sample. The coupon sample must then be pried open along the cut line and this can be carried out manually or with the aid of a tool such as a pair of pliers and a vise.

On the other hand, if the weld coupon sample is constituted of a relatively thick-walled tube, the prior art procedures favor slitting a single wall of the tube longitudinally so as to bisect the single tube wall through the weld area and then bending opening the tube by prying apart the tube ends along the cut line so that the tube is sprung open along the uncut tubular side wall. In either case, depending upon the strength of the metal forming the tubular weld coupon sample and its resistance to deformation, certification of tubular weld coupon samples may require considerable manual effort and dexterity that must be sustained in a repetitious pattern of preparation and inspection.

BRIEF SUMMARY OF THE INVENTION

The present invention entails a simple process of preparation of tubular weld coupon samples that avoids many of the problems encountered in using prior art procedures and facilitates both preparation and inspection procedures.

In accordance with one embodiment of the process according to the present invention, a sample of butt-welded tube lengths joined by a circumferential full depth weld is diagonally cut partially through its transverse dimension so as to leave an uncut circumferential bending strip having a circumferential length sufficiently less than the tube diametric dimension so as to enable bending the cut sample in an opening direction about the strip. The cutting step is carried out so that the cut intersects and severs the circumferential weld at at least one peripheral location and such that the cut diagonally extends from one axial side of the weld adjacent the weld to the other adjacent axial side of the weld.

In one specific embodiment of the process, the cutting step is carried out such that the cut intersects the weld only once and the bending strip intersects a portion of the weld. In accordance with another embodiment of the process, the cutting step is carried out such that the cut intersects the weld twice so as to sever the weld into two parts, with each part remaining with the sample on either side of the cut.

A jig fixture for use in carrying out the cutting procedure at least for carrying out one embodiment of the process according to the invention includes a base fixture on which is mounted a sample holder arranged to receive a tubular coupon sample extending lengthwise of the holder. A clamping arrangement secures the coupon to the sample holder and the sample holder is mounted for reciprocal feed motion relative to the base fixture transversely of the length of the coupon sample and the sample holder. The sample holder includes a feed limit device for limiting the feed motion distance of the sample holder relative to the base fixture from a starting position and also includes an elongate slot for permitting linear passage therethrough of a cutting blade. The lengthwise dimension of the slot extends parallel to the direction of the reciprocal feed motion of the sample holder. The base fixture includes a blade receiving opening aligned with the slot in the sample holder at least while the sample holder undergoes reciprocal feed motion relative to the base fixture.

The jig fixture is arranged to be mounted on a commercial band saw whereby the band saw blade will extend through the sample holder slot and the base fixture opening. Tilting of the base fixture and sample holder relative to the blade enables the coupon sample to be positioned for diagonal cutting part way through the tubular sample so as to leave a bending strip along one sidewall of the coupon sample.

The jig fixture in accordance with the invention permits simple safe cutting of tubular weld coupon samples diagonally through the transverse dimension of the sample so as to leave a bending strip along one sidewall of the sample so that the sample can be easily bent open about the length of the bending strip with a simple, expeditious maneuver.

The bending of the coupon sample above the bending strip is considerably easier than bending the entire sidewall of a coupon sample prepared in accordance with the prior art and offers significant advantages in an inspection operation where numerous coupon samples must be processed in rapid succession.

BRIEF DESCRIPTION OF DRAWINGS

With reference to the drawings:

FIG. 1 illustrates a method for preparing a welded tubular coupon for inspection and certification in accordance with a known prior art procedure;

FIG. 2 shows another process for preparing a welded tubular coupon for inspection and certification in accordance with another known prior art process;

FIG. 7 is a side elevation view of the apparatus shown in FIG. 6; and

FIG. 8 is a rear elevation view of the apparatus shown in FIGS. 6 and 7; and

FIG. 9 shows the invention used to cut a small diameter tubular coupon sample.

DETAILED DESCRIPTION OF PREFERRED EMBODIMENTS OF THE INVENTION

Figure 3:
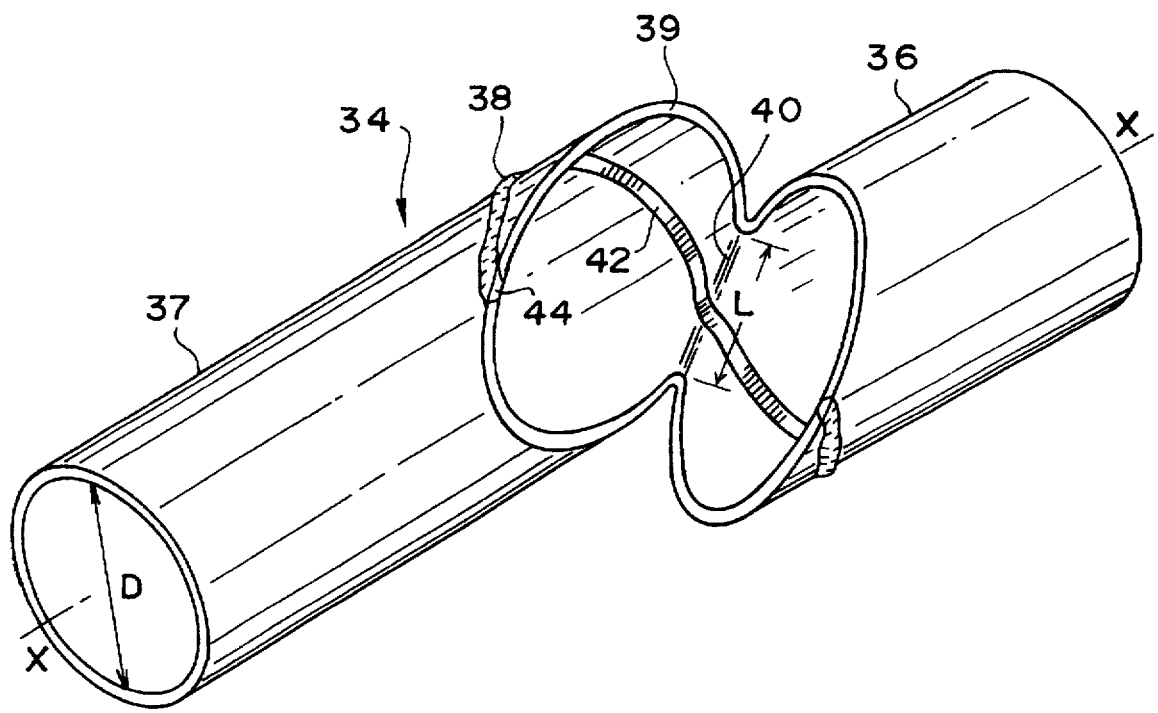
FIG. 3 shows a welded tubular coupon prepared in accordance with a first embodiment of the process according to this invention.

With reference to the appended drawings, FIG. 1 shows a tubular weld coupon sample 10 formed from two tubular lengths 12, 14 butt-welded together by a circumferential full depth weld 16 that extends circumferentially entirely around the butt-weld area and up to the internal circumferential area 18 of the coupon sample 10.

To prepare the coupon sample shown in FIG. 1 for inspection, the sample 10 has been longitudinally cut along line 20 essentially along the diameter of the sample so as to sever the sample and the weld area 16 along a plane extending essentially diametrically across the coupon sample. In accordance with the procedure illustrated in FIG. 1, the coupon sample 10 is then bent outwardly along the cut line 20 so as to expose the inner surface of the weld area 16 for visual inspection. It will be noted that the cut made along line 20 inherently removes a portion of the weld area 16 preventing inspection of the removed portion of the weld. Also, in accordance with this prior art procedure, the coupon must be readily deformable so as to permit bending outwardly of the split portions of the coupon quickly and usually by manual manipulation due to the large volume of coupons that are typically processed by an inspector during any inspection interval.

If tubular coupons to be inspected and certified have thick wall sections that prevent ready manipulation of the split portions of the coupon into an open position, the prior art process in accordance with FIG. 2 can be utilized, wherein a tubular coupon sample 22 comprising a pair of tubular lengths 24, 26 butt-welded circumferentially with a full depth weld 28 is prepared for inspection by longitudinally slitting one sidewall of the tubular coupon along cut line 30 and the cut sidewall is then sprung or bent outwardly as illustrated so as to expose the interior circumferential area 32 of the tubular coupon to thereby permit inspection of substantially all of the interior of weld 28. Obviously, the single cut along line 30 in the procedure illustrated in FIG. 2 removes less of the weld 28 then the procedure illustrated in FIG. 1 and bending open the coupon along the single cut line is facilitated when the thickness of the coupon wall renders the procedure in accordance with FIG. 1 difficult or time-consuming.

Figure 4:
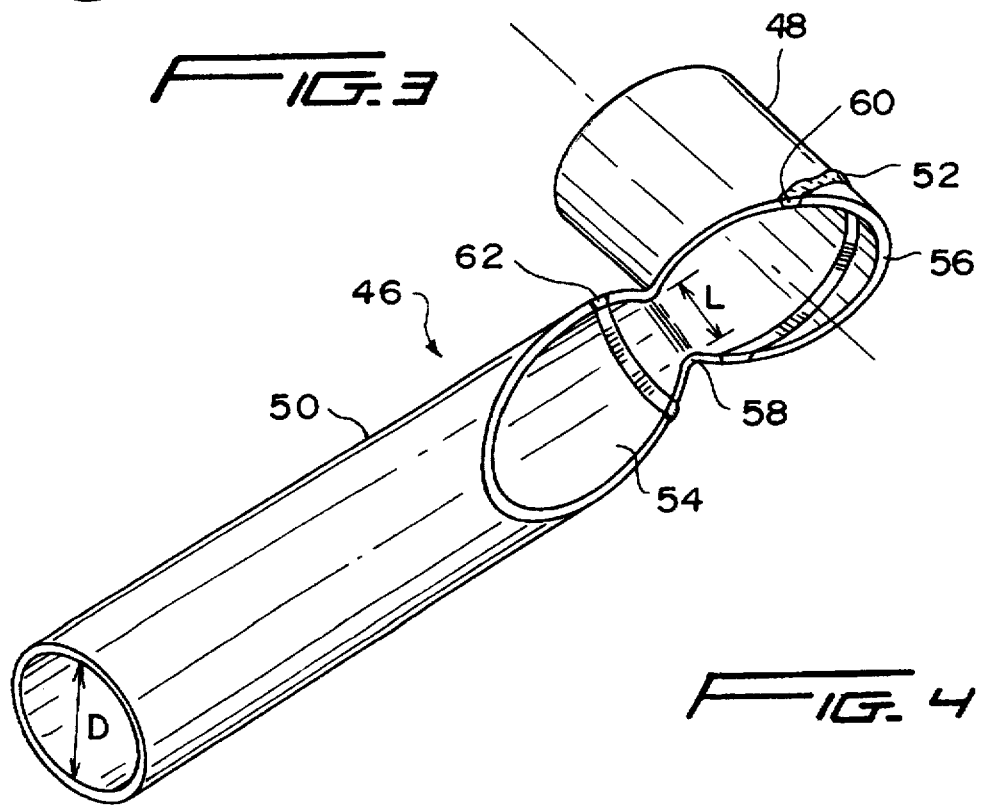
FIG. 4 shows an alternate embodiment of a method of preparing a tubular welded coupon for inspection and certification in accordance with an alternate embodiment of the process according to this invention.

An improved process according to the invention is illustrated in FIGS. 3 and 4 that simplifies tubular coupon preparation for inspection and facilitates opening of the cut coupon in easier fashion than the bending utilized in the prior art processes illustrated in FIGS. 1 and 2. With reference to FIG. 3, a first embodiment of the process for preparing a tubular weld coupon in accordance with the present invention is illustrated and involves diagonally cutting a tubular weld coupon 34 along cut line 39 from a sample of full depth butt-welded tube lengths 36, 37 welded along weld line 38 diagonally partially through its transverse dimension so as to leave an uncut circumferential bending strip 40 having a circumferential length L sufficiently less than the tube diametric dimension D so as to enable bending the cut sample in an opening direction about the bending strip 40. Upon bending of the sample about the cut line 40, the entire interior of the full depth weld along its inner circumferential area 42 is readily permitted.

The cut line 39 intersects and severs the circumferential weld 38 at at least one peripheral location 44 and leaves the remainder of the weld 38 available for inspection due to the fact that the diagonal cut is made such that the cut diagonally extends from one axial side of the weld adjacent the weld to the other adjacent axial side of the weld, as illustrated.

In accordance with an alternate embodiment of the coupon preparation process in accordance with the present invention, FIG. 4 illustrates a procedure for preparing a tubular weld coupon 46 from a sample of tube lengths 48, 50 butt-welded along a circumferential full depth weld 52 that extends to the interior circumferential area 54 of the coupon 46.

In accordance with the procedure illustrated in FIG. 4, the cutting step is carried out along cut line 56 such that the cut intersects the weld 52 twice so as to sever the weld into two parts as shown, with each part remaining with the sample on either side of the cut 56. Again, the cut line 56 in accordance with FIG. 4 extends diagonally through the coupon sample partially through its transverse dimension D so as to leave an uncut circumferential bending strip 58 having a circumferential length L sufficiently less than the tube diametric dimension D so as to enable bending the cut sample in an opening direction about the Length of the strip 58 for inspection, as illustrated. In accordance with the procedure illustrated in FIG. 4, the diagonal cut along line 56 is carried out so that the cut intersects and severs the circumferential weld 52 at two locations 60, 62 that leaves the two weld portions remaining with the sample on either side of the cut 56.

It has been determined from experimentation that, for smaller tubes, (i.e., less than about ¾ in.) the angle of the diagonal cut line 56 relative to the longitudinal axis x—x shown in FIG. 3 preferably will be on the order of 15°–20°, and up to about 45° for larger coupon samples exceeding about ¾ in. in diameter. The essential step is to diagonally cut through the sample sufficiently so as to leave a bending strip as illustrated at 40 or 58 in FIGS. 3 and 4 about which the tube can be readily pried open to permit inspection of the full interior length of the welds 38, 52. The Length of the bending strips 40, 58 is not critical except that this dimension must be sufficiently less than the diametrical Dimension of the coupon sample so as to readily permit opening of the cut sample about the length of the bending strip.

The coupon samples illustrated in FIGS. 3 and 4 are shown as being round, but it should be understood that this invention would apply equally in principle to a tubular coupon sample having any cross sectional shape, including square, oblong, elliptical, and other configurations. The expression "diametrical dimension" illustrated as "D" in the drawings is intended to denote a transverse dimension of the coupon sample for purposes of describing the principle of the process according to the present invention. Obviously, if the tube were square in cross section, the cut line in accordance with either procedure illustrated in FIGS. 3 and 4 would be at least up to one of the sidewalls of the coupon sample. The length L of the bending strip remaining on such a square cross-section coupon sample could correspond to a height dimension of one side of the coupon sample or the cut could be advanced on either side of the weld to shorten the length L to a sufficient extent to permit ready prying or bending open of the coupon sample after the diagonal cut has been made.

The apparatus for carrying out diagonal cutting of the coupon samples is not critical and any cutting apparatus that would create a cut line that would remove a minimal amount of weld is preferred. A commercial band saw has been found to perform the cutting operation in satisfactory fashion. However, any other cutting tool could be utilized to create the cut lines 39, 56.

The present invention also includes a jig fixture illustrated in FIGS. 5–8 for enabling diagonally cutting tubular coupons in accordance with the process described in FIG. 3. Essentially, the fixture described in FIGS. 5–8 is intended to be utilized with a continuous band saw wherein the fixture is mounted on the work table tilting pivots of the band saw so that any desired angle of diagonal cut can be made on a tubular coupon.

Figure 5:
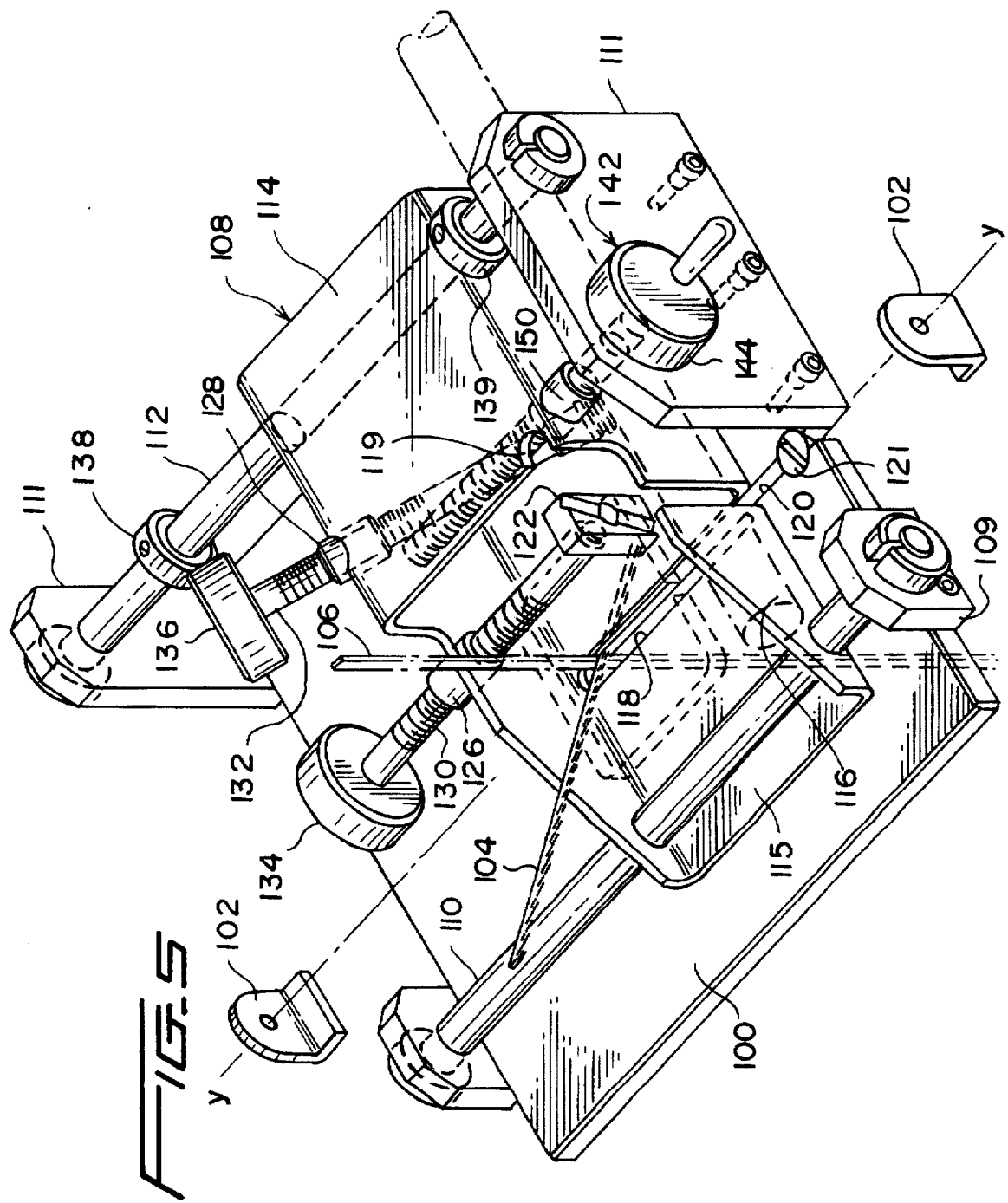
FIG. 5 is an isometric view showing apparatus for cutting a tubular welded coupon sample in accordance with the first embodiment of the process according to the invention.

More specifically, as illustrated in FIG. 5, a jig fixture for supporting a tubular coupon sample of the type illustrated in FIG. 3 comprises a base fixture 100 which is adapted to be mounted on the pivot supports 102 of a continuous band saw (not illustrated) so that the base fixture 100 can be tilted about an axis y—y relative to the blade 104 of the band saw on which the blade is mounted. The blade 104 in FIG. 5 is illustrated in full view in an inclined position relative to the base fixture 100 and is shown in hidden lines at 106 whereat the blade of the band saw extends perpendicular relative to the base fixture 100. In the position of the saw blade illustrated at 106, the base fixture 100 would not be tilted relative to the blade about axis y—y, whereas the position of the base fixture 100 relative to the saw blade as illustrated at 104 indicates it has been tilted about axis y—y in a manner that will be readily recognized and understandable to those skilled in the art of using band saws.

The base fixture 100 may be mounted to the pivot assembly 102 of a commercial band saw (not otherwise shown) after the tilt table of the band saw has been removed, or the base fixture 100 can otherwise be associated with the tilt table of a commercial band saw in a manner that will readily permit tilting of the base fixture 100 about axis y—y to produce a diagonal cut in the manner to be described below.

A sample holder 108 is mounted on the fixture base 100 by means of lo guide rods 110, 112 for transverse reciprocal feed motion in a direction essentially transversely of the length of the sample holder 108 (left to right in FIG. 6) and parallel to the axis y—y. Rods 110, 112 are secured to the base fixture by end fixtures, or sideplates 109, 111, respectively. The sample holder 108 in accordance with the preferred embodiment is constructed as a partially tubular member having parallel opposed upper and lower sidewalls 114, 115, respectively, and parallel opposed proximal and distal lateral sidewalls 116, 117, respectively, with the sidewalls 114, 115 extending perpendicular to sidewalls 116, 117, as best seen in FIG. 8. A small diameter coupon sample locating notch or groove 19 is provided in upper sidewall 114 of sample holder 108.

The tubular configuration of sample holder 108 constitutes the preferred embodiment of the sample holder in accordance with this invention but an open channel construction omitting the upper sidewall 114 and notch 119 could be used as well, provided that the structural rigidity of such configuration is sufficient to retain a coupon sample in position for cutting, as will be explained in more detail below. If an open channel is utilized for the sample holder 108, an appropriate marking or other indicia could be utilized to enable an operator to properly locate a small diameter coupon sample relative to sidewall 116 to enable cutting of the coupon sample by the cutting blade in the vertical position as shown at 106, as illustrated in FIG. 9. The use of the locating notch or groove 119 facilitates ready placement of a small diameter coupon sample C' as shown in FIG. 9 relative to the cutting blade 106 to permit a smaller angle diagonal cut through the coupon sample C' to minimize removal of weld material W' by blade 106. The clamping arrangement to secure the small diameter coupon sample C' in the position as illustrated in FIG. 9 will be described below.

The bottom sidewall 115 of sample holder 108 is provided with an elongate slot 118 for accompanying a saw blade 104, with the lengthwise dimension of slot 118 extending parallel to axis y—y so that reciprocal motion of the sample holder 108 along rods 110, 112 will cause the slot 118 to move lengthwise along axis y—y without interference with the blade 104. The blade 104, of course, has a cutting plane that includes and passes through the blade 104 along its cutting direction at the cutting zone of the blade whereby the cutting plane of blade 104 essentially extends along the slot 118.

Figure 6:
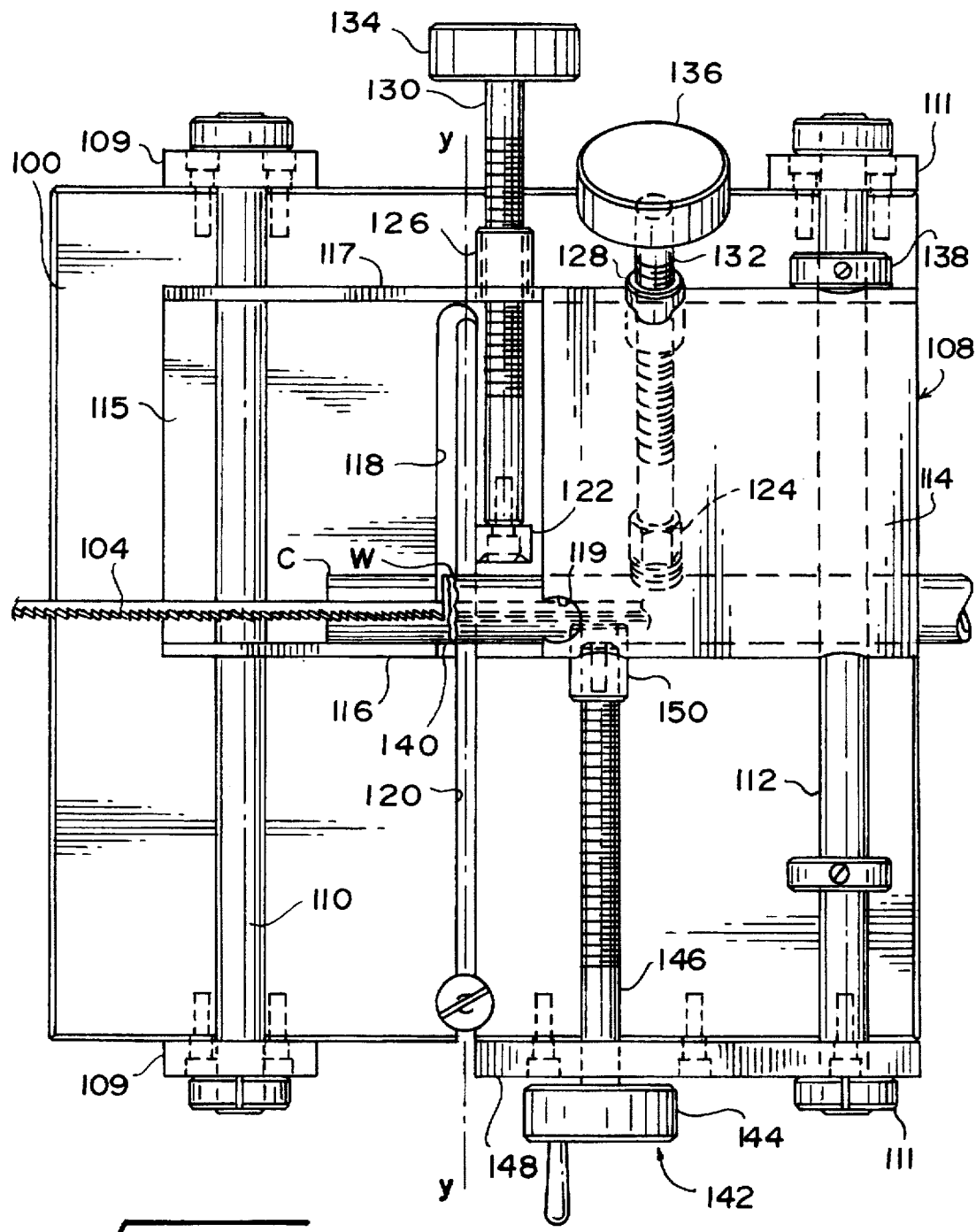
FIG. 6 is a top view of the apparatus shown in FIG. 5 with the saw blade located at a final cutting position following a diagonal cut partially through the coupon sample.

Base fixture 100 moreover, is provided with a saw blade receiving opening 120 also in the form of an elongate slot having its lengthwise dimension extending parallel with axis y—y. Saw blade 104 extends through the opening 120 in the base fixture and, as illustrated in FIG. 7, saw blade 104 also extends through axis y—y as well. Thus, with the base fixture 100 mounted for pivotal motion about axis y—y, saw blade 104 will not interfere with the base fixture 100 or sample holder 108 upon pivotal movement of those elements. As illustrated in FIG. 6, slot 118 in sample holder 108 is somewhat wider than the opening slot 120 in base fixture 100 because the sample holder 108 is elevated somewhat relative to axis y—y and base fixture 100 thereby requiring somewhat more clearance for blade 104 at slot 118 than at slot opening 120 to avoid interference between slot 118 and blade 104.

Both slot 118 and slot opening 120 are open at their proximal ends, which is toward the lower right as viewed in FIG. 5 and towards the bottom as viewed in FIG. 6. The open ends of the slots permits mounting of the base fixture 100 and its associated sample holder 108 onto a band saw with the saw blade 104 extending through the slots without the need to dismantle the saw blade and reassemble it in position within the slots. Thus, the base fixture 110 and its associated sample holder 108 can be assembled on a band saw tool for pivotal motion around axis y—y by simply passing the saw blade 104 through the slots 118, 120 during positioning of the base fixture 100. Obviously, slots 118 and 120 are aligned with but spaced apart from each other, as shown in FIG. 6. A screw clamp 121 may be used to close slot 120 (FIG. 5) and secure the free open sections on opposite sides of the slot against vibration and flexure.

A pair of coupon sample holding clamps 122, 124 are securely mounted on the sample holder 108 by means of threaded connections 126, 128, respectively. Screw threaded rods 130, 132 extend through the threaded connections 126, 128, respectively and include manipulating knobs 134, 136 for enabling rotation of rods 130, 132 to drive clamps 124, 126 in axial directions parallel to the rod lengths relative to the rods 130, 132. The rods 130, 132 are positioned such that the clamps 122, 124 can secure a coupon sample C (FIG. 8) in a corner area at the intersection of sidewalls 115, 116 or alternatively a small diametric coupon sample C' against a single sidewall 116, as shown in FIG. 9.

Thus, manipulation of knob 136 to rotate rod 132 will drive clamp 124 to secure a coupon sample C against the corner area between sidewalls 115, 116 as illustrated in FIG. 8 and manipulation of knob 134 will rotate rod 130 to drive clamp 122 towards and away from sidewalls 116 to secure a coupon sample C' against sidewall 116, if desired. In practice, smaller samples C', as shown in FIG. 9, will be mounted against proximal sidewall 116 and secured thereby by clamp 122. The base fixture 100 is adjusted so that the saw blade is located in the position as shown at 106 in FIG. 9, that is, essentially perpendicular relative to the base fixture 100. In this position, the small coupon sample C' is inclined such that the blade intersects the tubular coupon sample C' at a relatively small angle (i.e., 15°) relative to the longitudinal dimension of the coupon sample. This angle of partial cut diagonally through the coupon sample C' eliminates a minimum of weld material, considering the width of the blade 106 and the small diameter of the coupon sample. The use of the notch 119 enables placement of a small coupon sample C' in position ready for cutting, with the only requirement expected of the operator being to align the weld W' with the saw blade 106.

In accordance with the process of diagonally cutting a coupon sample in accordance with this invention, only a partial cut is made through the coupon sample C (or C') so as to leave a bending strip on a coupon as described previously in connection with the coupon preparation procedures illustrated in FIGS. 3 and 4. To ensure that the coupon C or C' illustrated in FIGS. 6, 8 and 9 is not cut entirely across its transverse dimension, an adjustable feed limit stop 138 is provided on rod 112 to limit the feed distance that may be traversed by the sample holder 108 on the guide rods 110, 112. The feed stop 138 is adjusted so that a coupon sample C as shown in FIG. 6 or C' as shown in FIG. 9 will not be cut entirely through its transverse dimension, but only up to a bending strip area illustrated at 140 in FIG. 6. In FIG. 6, the sample holder 108 is illustrated at its full limit of feed length whereat it is positioned against stop 138 with the coupon C having been fed against blade 104 at an angle relative to the blade as shown in FIG. 7 to produce a diagonal cut through the coupon C in the manner illustrated in FIG. 3. A motion stop 139 is also provided on the proximal area of rod 112 to establish the starting position or proximal position of sample notch 114 to avoid engagement between the sample notch and the saw blade 104, 106.

To achieve feed motion of sample holder 108, a feed screw device 142 includes a manipulating knob 144 and a feed screw 146 rotatably mounted in an end fixture 111 secured to base fixture 100. Feed screw 146 engages a threaded connection 150 in sidewall 116 of sample holder 108. Thus, in operation, manipulation of knob 144 rotates screw 146 to drive sample holder 108 along the guide rods 110, 112 in a direction extending longitudinally with respect to the feed screw 146, which also extends parallel to guide rods 110, 112. Rotation of screw rod 146, of course, advances or withdraws sample holder 108 along the rod 146 due to the connection between the threads of screw rod 146 and threaded connector 150.

Operation of the jig fixture is as follows. A larger diameter coupon sample C comprising two lengths of butt-welded tube elements joined together by a circumferential full depth weld is clamped in the sample holder 108 as illustrated in FIG. 6, with the weld line W appropriately positioned with respect to the slot 118. The stop 138 is positioned to limit the cut length through the coupon to leave a bending strip. The base fixture 100 is tilted relative to the saw blade 104 so that the cutting plane of the blade 104 will diagonally cut the coupon C through the weld line W as illustrated in FIG. 6, effectively bisecting the weld and producing a diagonal cut in the coupon corresponding to the cut shown in FIG. 3. Feeding of the sample holder 108 is achieved by manipulation of knob 144 so that the holder 108 is advanced until it reaches the stop 138 to thereby leave a bending strip 140 on the coupon. Following the cutting operation, the sample holder 108 is withdrawn from the blade area towards in starting position, the coupon is removed from the sample holder and is pried open using an appropriate tool or fixture for enabling a visual inspection as shown in FIG. 3.

For a smaller diameter coupon samples C', it is desired to decrease the cutting angle as compared with larger diameter samples to reduce the amount of weld removed by the saw blade, as discussed above. A cutting angle of about 15° relative to the longitudinal dimension of the coupon sample has been observed to produce a good coupon sample from a ¼ in. diameter thin walled tube sample, for example. The operator, of course, would have discretion in selecting the clamping arrangement to produce the best coupon sample.

The jig fixture illustrated in FIGS. 5–8 is adapted for use with a continuous band saw 104 but it will be understood by those skilled in the art that a reciprocating jigsaw (not shown) could be utilized as well with the same jig fixture. Also, the coupon sample holder 108 could be arranged such that a cut through a coupon sample would be made by clamping the coupon sample against the distal sidewall 117, reversing the saw blade 104, 106 and advancing the coupon sample against the saw blade from the proximal side of the coupon holder 108 towards the distal side thereof. The clamps 124, 122 and their associated rods and knobs would be reversed or another appropriate clamping means could be utilized, along with an appropriate feedstop device such that the coupon sample would not be cut entirely through its diameter in accordance with the inventive process described herein. Other equivalent variations of feed motion of sample holder 108 could be utilized by those skilled in the art without departing from the spirit and scope of the invention described herein and claimed below. Also, various clamping and feed screw devices, feedstop, slot configurations, cutting blades and other mechanical details described above in connection with the preferred embodiment of the invention could readily be substituted by equivalent mechanical devices known to persons skilled in the art without departing from the invention described herein and which is defined in the claims below.

What is claimed is:

1. A process for preparing a tubular weld coupon from a sample of butt-welded tube lengths joined by a circumferential full depth weld comprising:

diagonally cutting the sample partially through its transverse dimension so as to leave an uncut circumferential bending strip having a circumferential length sufficiently less than the tube diametric dimension so as to enable bending the cut sample in an opening direction about said strip;

carrying out the cutting step so that the cut intersects and severs the circumferential weld at at least one peripheral location and such that the cut diagonally extends from one axial side of the weld adjacent the weld to the other adjacent axial side of the weld.

2. The process as claimed in claim 1, wherein the cutting step is carried out such that the cut intersects the weld only once and the bending strip intersects a portion of the weld.

3. The process as claimed in claim 1, wherein the cutting step is carried out such that the cut intersects the weld twice so as to sever the weld into two parts with each part remaining with the sample on either side of the cut.

4. The process as claimed in one of claims 1, 2 or 3, wherein the cutting step is carried out such that the cut diagonally intersects the longitudinal axis of the sample at an angle of from about 15° to about 45°.

5. A process for preparing and inspecting tubular weld coupons comprising:

preparing a sample of welded tube lengths of given diameter by butt welding a pair of tube lengths together with full depth weld penetration;

diagonally cutting the sample partially through its transverse dimension so as to leave an uncut circumferential bending strip having a circumferential length sufficiently less than the tube diametric dimension so as to enable bending the cut sample in an opening direction about said strip;

carrying out the cutting step so that the cut intersects and severs the circumferential weld at at least one peripheral location and such that the cut diagonally extends from one axial side of the weld adjacent the weld to the other adjacent axial side of the weld;

bending the sample open along the bending strip so as to expose the interior of the weld along its entire circumferential length for visual inspection on either side of the cut;

visually inspecting the interior of the weld along its full circumferential length.

6. The process as claimed in claim 5, wherein the cutting step is carried out such that the cut intersects the weld only once and the bending strip intersects a portion of the weld.

7. The process as claimed in claim 5, wherein the cutting step is carried out such that the cut intersects the weld twice so as to sever the weld into two parts with each part remaining with the sample on either side of the cut.

* * * * *